United States Patent
Dukoff

(10) Patent No.: US 10,226,403 B2
(45) Date of Patent: Mar. 12, 2019

(54) COMPOSITION AND METHOD FOR USING MEDICAMENT FOR ENDODONTIC IRRIGATION, STEM CELL PREPARATION AND TISSUE REGENERATION

(71) Applicant: Amy Dukoff, New York, NY (US)

(72) Inventor: Amy Dukoff, New York, NY (US)

(*) Notice: Subject to any disclaimer, the term of this patent is extended or adjusted under 35 U.S.C. 154(b) by 141 days.

(21) Appl. No.: 15/627,760

(22) Filed: Jun. 20, 2017

(65) Prior Publication Data

US 2017/0304157 A1   Oct. 26, 2017

Related U.S. Application Data

(63) Continuation-in-part of application No. 14/592,148, filed on Jan. 8, 2015, now Pat. No. 9,730,862, which is a continuation of application No. 14/331,813, filed on Jul. 15, 2014, now Pat. No. 8,961,180, which is a continuation-in-part of application No. 13/954,434, filed on Jul. 30, 2013, now Pat. No. 9,717,657.

(60) Provisional application No. 61/717,691, filed on Oct. 24, 2012.

(51) Int. Cl.
*A61K 6/00* (2006.01)
*A61C 5/50* (2017.01)
*A61C 5/40* (2017.01)

(52) U.S. Cl.
CPC .............. *A61K 6/0035* (2013.01); *A61C 5/40* (2017.02); *A61C 5/50* (2017.02); *A61K 6/0032* (2013.01); *A61K 6/0041* (2013.01)

(58) Field of Classification Search
CPC .. A61K 6/0035; A61K 6/0038; A61K 6/0047; A61K 6/0041; A61K 6/0061; A61K 6/0064; A61K 6/0067; A61C 5/40–5/60; A61C 5/62

USPC .................. 433/224, 215, 81, 216
See application file for complete search history.

(56) References Cited

U.S. PATENT DOCUMENTS

| | | | | |
|---|---|---|---|---|
| 5,356,803 | A * | 10/1994 | Carpenter | A61K 8/43 435/200 |
| 6,878,287 | B1 * | 4/2005 | Marais | A61C 1/0076 204/554 |
| 2007/0275353 | A1 * | 11/2007 | Gharib | A61K 6/0008 433/224 |
| 2008/0193402 | A1 * | 8/2008 | Adamy | A61K 8/46 424/70.1 |
| 2008/0255498 | A1 * | 10/2008 | Houle | A61C 17/02 604/20 |

(Continued)

*Primary Examiner* — Yogesh P Patel
(74) *Attorney, Agent, or Firm* — Thomas A. O'Rourke; Bodner & O'Rourke, LLP

(57) ABSTRACT

A composition for tissue degradation and removal and disinfection is provided for dental and medical applications. It can function as a single intra-canal irrigant that eradicates microorganisms as it facilitates the debridement of a root canal system. It contains one or more hydroxides, a thioglycolate compound, sodium hypochlorite, sodium chloride, sodium chlorate, oxygen, and water, such as lime water and purified water, The thioglycolate compound is capable of degrading a cell by disrupting disulfide bonds in its proteins. The sodium hypochlorite enhances its function. The composition may also incorporate mineral oil, urea, cetearyl alcohol, D&C yellow No. 8, chromium hydroxide, theobroma cocoa seed butter, iron oxides, fragrances, lanolin, and/or ceteareth-20. It is effective against *Enterococcus faecalis*.

9 Claims, 8 Drawing Sheets

(56) References Cited

U.S. PATENT DOCUMENTS

| | | | |
|---|---|---|---|
| 2009/0208543 A1* | 8/2009 | Nathoo | A61K 8/02 424/401 |
| 2011/0302723 A1* | 12/2011 | Mansson | A61K 8/46 8/161 |
| 2013/0042421 A1* | 2/2013 | Smith | A61K 8/31 8/161 |
| 2015/0147718 A1* | 5/2015 | Khakpour | A61C 17/20 433/81 |
| 2016/0100574 A1* | 4/2016 | Pesaro | A01N 31/02 424/48 |

* cited by examiner

COMPOSITION AND METHOD FOR USING MEDICAMENT FOR ENDODONTIC IRRIGATION, STEM CELL PREPARATION AND TISSUE REGENERATION

CROSS-REFERENCE TO RELATED APPLICATIONS

This application is a continuation-in-part of U.S. patent application Ser. No. 14/592,148 filed Jan. 8, 2015 which is a continuation of U.S. patent application Ser. No. 14/331,813 filed Jul. 15, 2014 which is a continuation-in-part of co-pending U.S. patent application Ser. No. 13/954,434 filed Jul. 30, 2613, entitled "COMPOSITION AND METHOD OF USING MEDICAMENT FOR ENDODONTIC IRRIGATION, STEM CELL PREPARATIONS AND TISSUE REGENERATION" which claims the benefit of U.S. Provisional Application Ser. No. 61/717,691, filed Oct. 24, 2012, entitled "COMPOSITION AND METHOD OF USING MEDICAMENT FOR ENDODONTIC IRRIGATION, STEM CELL PREPARATIONS AND TISSUE REGENERATION." All of the foregoing are incorporated herein by reference in their entirety.

BACKGROUND

1. Field of the Invention

The present invention provides a novel composition and a novel method for irrigating unprepared and prepared surfaces for dental and medical procedures and, in particular, for an intra-canal medicament for endodontic irrigation, stem cell preparations, tissue regeneration, removal of smear layer, disinfection and removing pulpal tissue. The present invention provides a novel single medicament that is a bactericidal agent effective against microorganisms such as *Enterococcus faecalis*, *Streptococcus rnutans* and *Candida albicans*.

2. Description of the Related Art

Root canal treatment is required when tissues in root canals are injured, infected, inflamed irreversibly (pulpits), has abnormal growth, or is needed for restorative treatment. Bacteria destroys pulp (i.e., soft tissues occupying inner space of teeth) causing pulpal necrosis, inflammation (pulpitis), and internal granulomas or closed chronic granulomas pulpitis (i.e., abnormal growth of tissues due to bacteria and inflammation).

Pulpal inflammation including inflammation caused by microorganisms such as bacteria and fungi requires root canal therapy to eliminate these microorganisms. The root canal treatment is performed in order to remove bacteria, debris, tissues, calcifications, and organic matter from the root canal and then filling the space in order to prevent bacterial invasion and irritation into surrounding tissues. A failed root canal treatment is caused by the microorganisms that contaminate a root canal system when the microorganisms leak out from the root canal into surrounding bones which is called an apical periodontitis (i.e., apical inflammation around root apex). Typically, the dominant microorganism present in the apical periodontitis is *Enterococcus faelcalis* and is also one of the most commonly isolated bacteria in root canal infections.

The success of root canal (or endodontic) therapy is dependent on the removal of all tissues, debris and microorganisms from the root canal area. Treatment complication or failures may occur if pulpal tissue, infecting bacteria, and microorganisms are not eliminated completely from the root canal space and/or the dentinal tubules. Bacterial invasion of microscopic spaces in dentin, irregularities or imperfections in the dentin structure including isthmuses, ramifications, accessory canals, complex root canal systems and apical deltas, can further complicate the root canal treatment and its outcome. Pulpal calcifications, pulp stones, and calcified canals may prevent a practitioner from removing all the pulpal tissue in the root canal space affecting the success of the root canal treatment. Also, biofilms (i.e., layers of microorganisms, proteins, and polysaccharides) and a smear layer (debris from mechanical preparations) needs to be removed with all of its microorganisms eradicated. Root canal treatment is indicated to remove abnormal growth of pulpal tissue of pulp polyps (chronic hyperplastic pulpitis) and of granulomatous tissue of internal resorption caused by bacteria and inflammation.

Bacteremias, caused from the presence of bacteria in the blood after dental procedures, are a major concern to the American Dental Association (ADA), and the American Association of Orthopedic Surgeons (AAOS). The bacteria that are prevalent in endodontic infections may also cause bone infections, and both the ADA and the AAOS recommend prophylactic antibiotics to be given to patients in certain cases (e.g. total hip replacement) to prevent bacteremia and infection following denial procedures. Presently, the guidelines have changed and therefore, an orthopedic implant does not routinely require pre-medication. However, the guidelines do recommend that each patient should be evaluated based on the need for prophylactic antibiotics on a case by case basis by their dental and medical professionals.

The bacteria, *Streptococcus mutans* and *Enterococcus faelcalis*, which are prevalent in endodontic infections, are also prevalent in infections in the bones. The fungus *Candida* has also been found in the infections in the bones. In addition, *Streptococcus mutans* is one of the leading causes of infective endocarditis. Therefore, both the ADA and the American Heart Association (AHA) recommend antibiotic prophylaxis for those dental patients that may be at a risk for developing an infection when the *Streptococcus mutans* enters their blood streams following the dental procedures and causes bacteremia. There is a documented case in 'Heart Lung' publication on May 7, 1988, of *streptococcus mutans* that causes a hematagenous bone infection in lumbar vertebrae. Therefore, it is important to eradicate bacteria and fungi from the pulpal cavity to aid in preventing the formation of bacteremia after the dental procedures. Further, it is important to eradicate these microorganisms not only from the tooth but also from within a bony cavity or from an orthopedic prosthesis for maintaining the health of the patient. However, currently, there is no single medicament or irrigant that is bactericidal against *Streptococcus mutans*, *Enterococcus faelcalis*, and *Candida*.

Currently, the practitioner uses many types of irrigants in order to chemo-mechanically prepare the root canal system for obturation and regeneration of the tissues. The present endodontic treatments require use of a combination of medicaments and irrigants for the chemo-mechanical instrumentation, cleansing, disinfection, and preparing a site for endodontic regeneration. Some endodontic irrigants are utilized for their tissue dissolving ability. For example, sodium hypochlorite is a widely used tissue dissolving agent. Sodium hypochlorite's effectiveness is dependent on its concentration and irrigation time and is highly effective at 525% for 40 minutes and ineffective at 1.3-2.5%. However, Sodium hypochlorite tends to soften the dentin which is a contraindication for its prolonged use. Further, antibacterial agents are either bactericidal or bacteriostatic. For example, chlorohexidine is bactericidal while a mixture of tetracycline, an acid, and a detergent (MTAD) is bacteriostatic. Furthermore, other endodontic irrigants are chelating agents like Ethylenediaminetetraacetic acid (EDTA) that remove the smear layer and decalcify dentin. In endodontic regeneration, Triple Antibiotic Paste (TAP), a combination of metronidazole, ciprofloxacin, and minocycline, is used for intracanal disinfection which is effective at a high concentration but causes discoloration. Also, Double Antibiotic Paste (DAP), a mixture of metronidazole and ciprofloxin, is used during the endodontic regeneration due to, its antibacterial properties but it also causes discoloration. Further, calcium hydroxide paste is used for its alkaline property but is ineffective in eradicating endodontic pathogens. As discussed above, the success of the root canal treatment is dependent on removing all the contents from within the root canal system before obturation. As the American Association of Endodontists (AAE) stated in 2011, in "Endodontics: Colleagues for Excellence", "the search for an ideal material and/or technique to completely clean infected root canals continues".

Pulp calcifications within the root canal systems are obstructions to debridement in a variety of forms. Pulp stones are isolated areas of calcifications. While other calcifications take the form of diffuse calcification and irregular linear calcifications. Calcifications and calcification blockages present a problem for the practitioner in order to successfully negotiate the canal during instrumentation. Pulpal calcifications prevent root canals to be accessed and located. Pulpal calcifications can block the canal and prevent complete instrumentation of the canal space.

Conventional endodontic, intra-canal medicaments have specific limitations. For example, sodium hypochlorite and calcium hydroxide do not have the ability to eradicate all the bacteria in the root canal system. Sodium hypochlorite and calcium hydroxide need to be in direct contact for it to be effective but this is difficult to attain. The direct contact cannot be gained when there are calcifications present that are natural obstructions. Also, when chlorohexidine is mixed with sodium hypochlorite during the instrumentation, an orange-brown precipitate is formed that is hard to remove and can stain.

As another example, sodium hypochlorite can dissolve organic tissue by disrupting the cell's metabolism and its ability to function, but cannot predictably inactivate endotoxins. Also, sodium hypochlorite loses its effectiveness when it is diluted. Furthermore, it is irritating to tissues. Sodium hypochlorite is not effective against bacteria such as enterococcus faecalis in the biofilms. Calcium hydroxide, an intra-canal medicament, has some antibacterial effect but is ineffective against the enterococcus faecalis, which is the most commonly isolated microorganism found in periapical lesions of the failed root canal treatment procedures.

Additionally, ethylenediaminetetraacetic acid (EDTA) which is water soluble is effective for removing inorganic material as a chelating agent but not as an effective antibacterial agent. However, EDTA should not be used with sodium hypochlorite, as it reduces the available chloride making sodium hypochlorite not effective as an irrigant.

MTAD is a mixture of doxycycline, citric acid, and Tween 80 (a detergent) in order to remove some, of the smear layer. However, it is not effective against fungi within the root canal system. Also, it can have a negative effect on the bond strength of root canal sealers when used as a final intra-canal rinse. Additionally, chlorhexidine or clorhexidine digluconate that are both water soluble can be used for disinfection but cannot dissolve tissue.

Pulp tissues contain disulfide bonds that are derived by coupling of two thiol groups, The linkage is called as an SS bond or disulfide bridge. When the disulfide bonds are broken, cell death or apoptosis occurs. Apoptosis is needed to eradicate bacteria from the root canal during the chemo-mechanical instrumentation and to prevent bacteria from re-infecting the root canal and causing apical periodontitis. Disulfide bonds are present in bacteria as they serve as a protective role for bacteria. Further, in humans also, disulfide bonds are found in secretory proteins, lysosomal proteins, mRNA, red blood cells, white blood cells, hematopoeisis cells, fibronectin, blood vessels, immunoglobins macrophages, neutrophils, membrane proteins, antibodies, and exoplasmic domains of membrane proteins in endoplasmic reticulum. Further, disulfide bonds are also found in nuerokeratin of the myelinated sensory nerve A fibers that can be found in the pulpal tissue. Disulfide bonds are needed for protein folding. Disulfide bond formation takes place in the endoplasmic reticulum. The soft tissue of the bony cavity contain hematopoesis cells, red blood cells, white blood cells, and blood vessels which contain disulfide bonds.

Traditionally, the dental professional or practitioner prepares a root canal system by chemo-mechanically debriding the tissue, debris and microorganisms with the use of irrigants and medicaments. The practitioner in order to clean, debride, disinfect, and shape the pulp chamber needs to dislodge calcifications, remove pulpal tissue, remove debris, and eradcate microorganisms that are present. The dental professional uses multiple medicaments and irrigants but none of the conventional irrigants or medicaments is able to eradicate *Enterococcus faecalis* successfully as a single intra-canal medicament. Likewise, in a bony cavity the soft tissue that needs to be removed is done with the intramedullary reaming which is similar to the removal of pulpal tissue by reaming during instrumentation.

Thus, there is a need for a composition and method that can more effectively and more efficiently dissolve tissues, remove debris, remove the smear layer, disinfect, eradicate microorganisms and dislodge calcifications in the root canal treatment, for preparing surfaces for stem cell therapy, and for endodontic tissue regeneration. Further, there is also a need for a single intra-canal medicament that is a bactericidal agent that eradicates *Enterococcus faecalis* without affecting the micro hardness of dentin and which works within a short time.

SUMMARY OF THE INVENTION

The present invention addresses the needs presented above by providing, in its various embodiments, novel compositions that are capable of tissue dissolution, disinfection, tissue degradation, tissue removal, disruption of cellular function, and also effective methods of using such compositions, as well as systems for treating patients which use these compositions.

In one aspect, the present invention relates to a method of treating a patient that includes the irrigation of a bony cavity within a tooth with a thioglycolate-containing composition according to the invention and the removal of pulpal tissue from the bony cavity. Irrigation of the cavity involves, in some cases, flowing the composition into the pulpal cavity (for instance, through a syringe and endodontic irrigation needle or curved syringe tip familiar to those skilled in the art) and removing it from the cavity. Alternatively or additionally, irrigation of the cavity is achieved by coating part of a medical instrument with the composition and then inserting the coated portion into the bony cavity.

The composition according to the invention containing thioglycolate used in these methods can be adapted to disrupt disulfide bonds in soft tissues and/or microbes (i.e. non-human microorganisms). When in use, the composition may contact a surface of the bony or pulpal cavity for various intervals, for example 30 seconds, 1 minute or 2 minutes more or less, etc., and may contact inner surfaces of the pulpal cavity that include those most proximate to the root apex.

In various embodiments, the composition according to the invention includes a thioglycolate such as sodium or potassium thioglycolate, sodium hypochlorite, sodium chloride, oxygen, sodium chlorate, calcium hydroxide, and water, especially lime water and/or purified water, formulate so that the composition controls and eliminates tissues, affected by abnormal growth as in pulpitis, infected tissue, and in granulomas. Hydroxides are typically present in various amounts in sufficient concentrations within the composition to deprotonate the thioglycolate and/or a biomolecule in soft tissue.

The sodium hypochlorite present in the composition for tissue dissolution, disinfection, tissue degradation, tissue removal, disruption of cellular function according to the present invention enhances the ability of the thioglycolate to disrupt disulfide bonds in soft tissues and/or in proteins present in various microbes in addition to its own tissue destroying action. Sodium hypochlorite requires over 20 minutes to be antimicrobial however after 20 minutes, sodium hypochlorite causes dental demineralization. The present invention shortens the working time of sodium hypochlorite to under 20 minutes which is beneficial to preserving the mineral content of the dentin of the root. The composition is thus especially effective as a bactericidal agent because of the presence of both thioglycolate and hypochlorite working together shorting the reaction time benefiting the patients treatment.

The sodium chloride present in the composition interferes with membrane permeability, causes changes in a cell's metabolism, alters the cell's ability to function and changes the cell size by introducing osmotic stress to, facilitate debridement. The small amount of oxygen, in the composition can also react with cell membranes and disrupts the cell functions. Sodium chlorate is known as an antiseptic agent.

U.S. Pat. No. 8,808,718 discloses an antimicrobial composition for endodontic or periodontal treatments and surgery comprising inorganic acids, and/or salts thereof and optionally inorganic salts, such as sodium chloride, but is silent regarding thioglycolic acid or its alkali metal salts in particular. Both sodium chloride- and calcium hydroxide-containing compositions were tested against $E.\ faecalis$ and $P.\ aeruginsa$ for their effectiveness against these microorganisms. U.S. Pat. No. 8,808,718 does not disclose or suggest an antimicrobial composition for endodontic or periodontal treatments that contains reducing compounds, which attack the disulfide bonds in proteins found in such microorganisms, such as potassium or sodium thioglycolate, together with alkali metal hypochlorite salts, but does teach that sodium hypochlorite is a potent disinfectant for periodontal and endodontic applications, which attacks and destroys the organic matter of tissues. Thus the aforesaid U.S. Pat. No. 8,808,718 does not disclose or suggest the above-described the compositions for tissue dissolution, disinfection, tissue degradation, tissue removal, disruption of cellular function according to the present invention.

The present invention encompasses other methods as well. For instance, certain methods according to the invention involve irrigation of a bony cavity with a composition according to the invention that includes one of the following reducing agents for breaking or disrupting disulfide bonds: potassium thioglycolate, calcium thioglycolate, 2-mercaptoethanol, dithiothreitol, dithioerythritol, tris(2-carboxyethyl)phosphine, dithiobutylamine, and glutathione, together with sodium hypochlorite, sodium chloride, oxygen, sodium chlorate, calcium hydroxide, and water, especially lime water and/or purified water. Irrigation of the bony cavity (which may include, for example, the pulpal cavity of a tooth, or a cavity generated or enlarged during the operative removal of a carious lesion of the tooth) with this composition degrades tissues and/or microbes (e.g. bacteria, viruses and fungi) within the bony cavity. As described above, irrigation of the cavity generally involves flowing the composition into the bony cavity (e.g. through a syringe and endodontic irrigation needle or syringe tip) and removing it from the cavity, or coating part of a medical instrument with the composition and then inserting the coated portion into the bony cavity. And, as above, the composition according to the invention may contact a surface of the bony cavity for intervals that include, without limitation, 30 seconds, 1 minute or more, 2 minutes or more or less. The composition optionally contacts inner surfaces of the bony cavity that include those most proximate to the root apex.

Other embodiments of the composition according to the invention for tissue dissolution, disinfection, tissue degradation, tissue removal, disruption of cellular function and antimicrobial action additionally comprise a fragrance-imparting compound, lanolin, mineral oil urea, ceteryl alcohol and ceteareth-20.

In some embodiments the composition for tissue dissolution, disinfection, tissue degradation, tissue removal, disruption of cellular function is bactericidal and able to reduce the quantity of $E.\ faecalis$ by 99% or more (e.g. 99.9%), so that in some cases, the composition can be used as a restorative dental rinse to aid in, cleansing the surface of the dentin to aid in preventing recurrent infections.

Preferred embodiments of the antimicrobial composition for tissue dissolution, disinfection, tissue degradation and tissue removal according to the present invention contain from about 0 2% to about 6% sodium hypochlorite (NaOCl) by weight, from about 0.05% to about 2% of potassium thioglycolate by weight, and from, about 0.005 to about 8.0%, preferably about 0.008% of calcium hydroxide by weight. The solution remains effective as long as there are negligible amounts of NaClO3. As pH is lowered below 11, significant amounts of NaOCl decompose to form NaCl, Na ClO$_3$ and small amounts of O$_2$ in the composition of the invention which benefits the effectiveness of thiocoglycolate. Hence the composition according to the present invention is known to contain at least some sodium chloride and sodium chlorate as well as small amounts of oxygen as well as the sodium hypochlorite when it is used. Furthermore the amounts of these products in the composition can vary in the composition due to sodium hypo chlorite's rate of decomposition and pH while it sits prior to use. Higher concentrations of hypochlorite result in faster decomposition so that a 15% solution decomposes 10× faster than a 5% solution. The decomposition rates increase with increasing temperature.

During use in the methods according to the present invention the composition for tissue dissolution, disinfection, tissue degradation and tissue removal has a pH of about 5.5 to about 8. However when first prepared a solution of about 6.5% sodium hypochlorite, about 0.01% Calcium hydroxide, and about 1% potassium thioglycolate in purified water has a pH of about 8, but about 3 weeks later it had a pH of about 6.5 and a taste similar to table salt.

Other methods encompassed by the invention include the steps of forming an access opening to expose a bony cavity within a tooth, irrigating the bony cavity that includes a reducing agent effective in disrupting disulfide bonds in proteins, debriding the cavity and rinsing it to remove the composition, and filling the bony cavity with an inert filling (e.g. gutta-percha and/or cement). The various embodiments of these methods can include the various optional features described above.

In another aspect, the present invention relates to methods of treatment of inner surfaces of bony cavities more generally. Bony cavities may exist in any osseous tissue including, without limitation, teeth, long bones, compact bone, spongy bone, and combinations thereof. These cavities may be naturally occurring (e.g., due to bone cysts) or man-made (e.g. voids left after resection of tumors or for implants). These methods generally involve contacting pulpal tissues and/or microbes within the bony cavity with a composition that includes, in various embodiments, one or more of potassium thioglygolate, calcium thioglycolate, 2-mercapto ethanol, dithiothreitol, dithioerythritol, tris(2-carboxyethyl) phosphine, dithiobutylamine, and glutathione. Contacting materials (e.g. pulpal tissues, microbes and biofilms) within the bony cavity with the composition disinfects the bony cavity and/or disrupts a tissue within the cavity.

In still another aspect, the present invention relates to a composition for dissolving tissues, disinfecting, deodorizing, degrading tissues, and removing tissue smear layer from a root canal treatment and within a bony cavity. The novel composition of the present invention includes calcium hydroxide, sodium hydroxide, potassium thioglycolate, sodium hypochlorite, sodium chloride, oxygen, sodium chlorate, water, mineral oil, urea, cetearyl alcohol, lanolin, aloe, fragrance, and ceteth-20, such that, the composition disrupts cellular functioning in at least one of infected tissues, inflamed tissues, and pulpal tissues affected by abnormal growth, such as, in neoplasms.

The present invention further provides a novel composition of matter used for tissue dissolution, tissue degradation, disinfection, deodorize, lubricate, chelation, removal of tissue in a hard bony cavity, and preparing the hard bony cavity for placement of stem cells and allow for tissue regeneration. The composition of matter Includes calcium hydroxide, sodium hydroxide, sodium hypochlorite, sodium chlorate, sodium chloride, potassium thioglycolate, water, mineral oil, urea, cetearyl alcohol, and ceteth-20, such that, the novel composition for use within a bony cavity degrades pulpal, inflamed tissues, and tissues affected by abnormal growth in neoplasm and in infected tissues with microorganisms.

Further, the present invention novel, use can provide a number of advantages, First, embodiments, of the present invention provide a novel composition and a novel method for using a chemical depilatory for endodontic usages. The present invention utilizes the ability of the chemical depilatory to break disulfide bonds in the tissues of pulpal area. By breaking the disulfide bonds, the chemical depilatory provides for weakening the structure of the pulpal tissue. Further, the present invention provides a composition that provides effective and quick results as seen in apoptosis of bacteria in data from the experiments performed in the present invention. The chemical depilatories work at a fast rate of within five minutes. The present invention's additional components function to decrease the thioglycolate's time needed to be effective. In addition, the present invention is capable of functioning without causing dentin demineralizaton. The chemical depilatory's ability to be effective within minutes of its application provides an advantage in patient care as patients can keep their mouth open for a limited time as the composition is applied to soft tissues of the infected area. Further, tissues with granulomas are caused due to infections. The present invention provides a novel depilatory having applications in dentistry and medicine. The present invention novel use of the depilatory's keratin-degrading has the ability to break the disulfide bonds to interfere with a cell's ability to function, survive, and perpetuate in the pulpal tissue, infected tissue and tissue with abnormal growth. The present invention's novel use of breaking of the disulfide bonds in the pulpal tissue, infected tissue, and tissue with abnormal growth that disrupts the cell's ability to survive causing apoptosis, and cell death in bacteria, yeast, and microorganisms. The present invention additional components aid in disrupting the cell's function which allows the chemical depilatory time needed to be effective to be less.

Also, the present invention's depilatory is an intra-osseous irrigant that is bactericidal for use against the microorganisms of *Enterococcus faecalis*. Next, the present invention combines multiple applications into a single medicament that can be used in the root canal treatments on all types of tissue such as, but is not restricted to, abnormal, inflamed, normal and infected tissues. The present invention is a chemical depilatory that breaks disulfide bonds by direct contact application on all types of tissues that have disulfide bonds that are in a bony cavity. As is well known to those of skill in the art, disulfide bonds are often critical to the proper folding and function of proteins.

Further, regenerative endodontic utilizes irrigants, antimicrobial agents, and antibacterial agents on necrotic pulpal tissue for disinfection and cleansing of the site so that regeneration occurs. The present invention combines irrigants and antimicrobial agents into one composition for its use in endodontic regeneration for placement on the site for regeneration. Further, the composition and the method are capable of removing debris that is formed during dental procedure and dissolving proteins along with calcifications within the pulpal chamber. Furthermore, the present invention provides a composition that is also capable of bleaching teeth.

Further, the present invention novel use provides a method that integrates many processes to be effective at same time. The present invention novel use of a chemical depilatory in endodontic facilitates the removal of pulpal tissue and, bacteria and microorganisms. The novel use of the chemical depilatory in endodontic facilitates removal of contents within the root canal treatment as it lubricates, irrigates, disinfects, dissolves, cleanses, deodorizes and removes the smear layer. Further the chemical depilatory has antimicrobial benefits. The novel use of the present invention utilizes the chemical depilatory in a sodium hypochlorite solution with additional components as a single irrigant that combines tissue dissolving ability and smear layer removal capacity with antibacterial properties. Further, the present invention facilitates breaking glycosaminoglycans (GAG) bond within the smear layer and facilitates its removal. Also, the present invention novel use utilizing the chemical depilatory's ability to break disulfide bonds present in proteins, Deoxyribonucleic acid (DNA), Ribonucleic acid (RNA), neoplastic and pulpal cells to further disrupts the ell's ability to function. Further, the present invention, novel method and use dislodges pulpal calcification by breaking the bonds in the tissue surrounding it. Next, the present invention novel method and use dissolves, removes and degrades tissues within the body that has abnormal growth as in neoplasm as granulomas and/or infected tissues that includes bacteria, fungi (yeast), and microorganisms.

Further, the present invention in a novel method utilizes a chemical depilatory for removal of tissues from within a hard bony cavity. The present invention utilizes the chemical depilatory in combination in a solution with sodium hypochlorite, sodium chloride and sodium chlorate in the novel method and application and use for removing a soft tissue, necrotic tissue, debris, and calcified tissue from within the hard tissue cavity with having the ability to do so within 5 minutes. Further, the present invention provides a composition that is effective on unprepared tooth surfaces as well as on prepared tooth surfaces. Furthermore, the composition, provided by the present invention, is useful in medicine, especially in long bones, in preparing skeletons for museums etc. More generally, compositions and methods according to various embodiments of the invention are useful in any setting where the removal of organic tissue and the sparing of bony tissue is desired.

These and other advantages will be apparent from the disclosure of the present invention contained herein.

The preceding is a simplified summary of the present invention to provide an understanding of some aspects of the present invention. This summary is neither an extensive nor exhaustive overview of the present invention and its various embodiments. It is intended neither to identify key or critical elements of the present invention nor to delineate the scope of the present invention but to present selected concepts of the present invention in a simplified form as an introduction to the more detailed description presented below. As will be appreciated, other embodiments of the present invention are possible, utilizing, alone or in combination, one or ore of the features set forth above or described in detail below.

BRIEF DESCRIPTION OF THE DRAWINGS

The above and still further features and advantages of the present invention will become apparent upon consideration of the following detailed description of embodiments thereof, especially when taken in conjunction with the accompanying drawings, and wherein.

Figure 1:
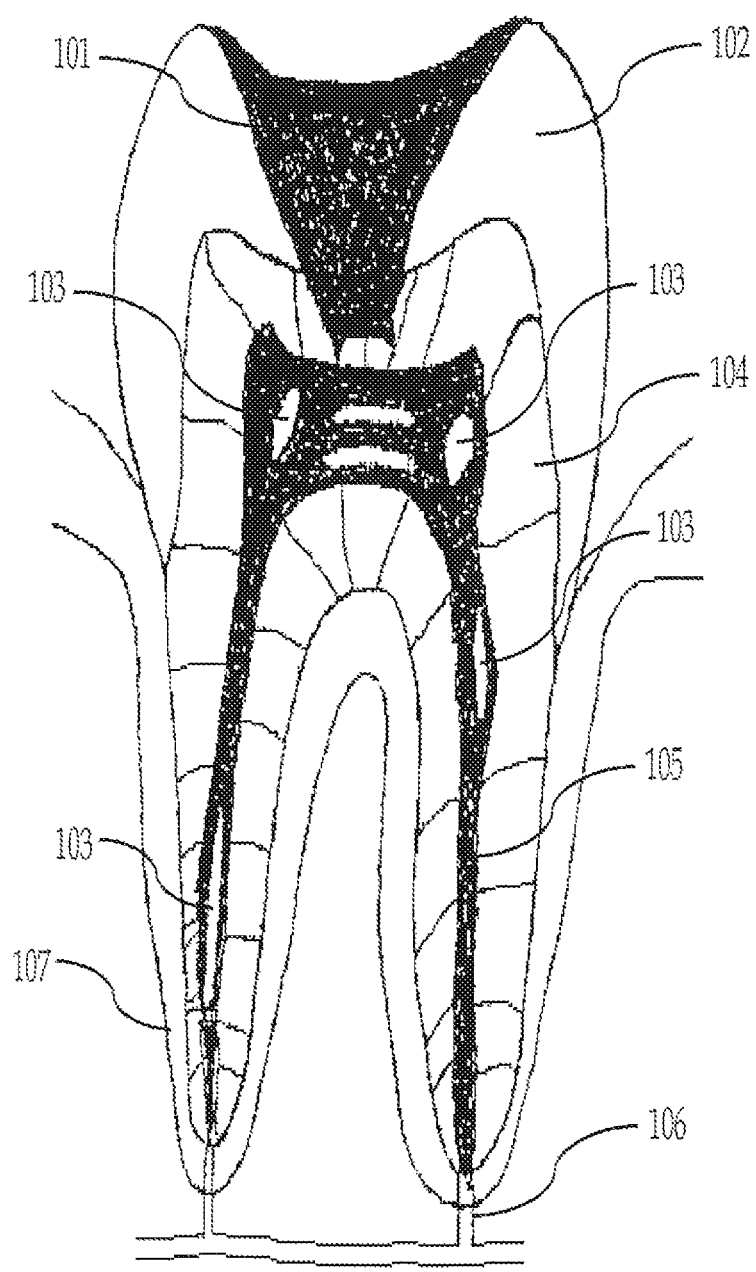
FIG. 1 is a cross sectional view of a tooth with tooth decay about to go under treatment in accordance with an embodiment of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including but not limited to. To facilitate understanding, like reference numerals have been used, where possible, to designate like elements common to the figures.

DETAILED DESCRIPTION

The present invention will be illustrated below in conjunction with an exemplary application, e.g., root canal treatment. Although well suited for use with, e.g., a medical application having disulfide bonds and requiring breakage of disulfide bonds, the present invention is not limited to any particular type of medical application. Those skilled in the art will recognize the disclosed techniques may be used in any medical or non-medical application in which it is desirable to provide breakage of disulfide bonds.

The phrases "at least one", "one or more", and ""and/or"" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The terms "determine", "calculate" and "compute," and variations thereof, as used herein, are used interchangeably and include any type of methodology, process, mathematical operation or technique.

In the following detailed description numerous specific details are set forth in order to provide a thorough understanding of embodiments or other, examples described herein. In some instances, well-known methods, procedures, compositions, or components have not been described in detail, so as to not obscure the following description. Further, the examples disclosed are for exemplary purposes only and other examples may be employed in lieu of, or in combination with, the examples disclosed. It should also be noted the examples presented herein should not be construed as limiting of the scope of embodiments of the present invention, as other equally effective examples are possible and likely.

FIG. 1 shows a cross-sectional view of a tooth 100 in accordance with an embodiment of the present invention. The tooth 100 includes tooth decay 101, as shown in the figure. Because of the tooth decay 101, the tooth 100 is under a treatment (i.e., root canal treatment). The tooth 100 further includes enamel 102, a pulpal calcification 103, dentin 104, and a pulp 105. The tooth 100 further includes an apex 106 and a periodontal ligament 107. The purpose of the root canal treatment is to completely remove the pulp 105 (as it is infected or injured, and can infect surrounding teeth), and that includes removal of all tissues, debris and microorganisms from root canal area.

Tissues of the pulp 105 differ from tissues of the enamel 102 and tissues of the dentin 104. Pulpal tissue is a highly vascular and soft tissue. On other hand, the dentin 104 and the enamel 102 are hard, calcified, and mineralized tissues. The enamel 102 and the dentin 104 include same type of inorganic materials, but differ in degree of calcification and mineralization of the inorganic material. Further, protein of the enamel 102 is resistant to enzymatic hydrolysis. The enamel 102 is more resistant to enzymatic digestion than skin. Therefore, the protein of the enamel 102 is not classified as a type of keratin and is not affected by actions of a chemical depilatory, if the chemical depilatory is applied. Further, chemical composition of the tissues of the pulp 105 is different than chemical composition of the dentin 104 and the enamel 102.

According to an embodiment of the present invention, the pulp 105 includes disulfide bonds. The disulfide bond is a covalent bond that is derived by coupling of two thiol groups. The linkage is called an SS bond or disulfide bridge. The disulfide bonds are present in a plurality of living and non-living species. For example, disulfide bonds are present in bacteria as they serve as a protective role for bacteria. Further, in humans also, disulfide bonds are found in secretory proteins, lysosomal proteins, and exoplasmic domains of stability of proteins in, extracellular tissue. Further, disulfide bonds are also found in neuro-keratin of the myelinated sensory nerve A fibers. Furthermore, disulfide bonds are present in HNGB1 (high-mobility group protein-1), which is a mediator of inflammation. According to an embodiment of the present invention, a method is provided for utilizing the disulfide Bond or S—S bond for cleaning out the pulp 105 and removing tissue.

Tissues of the pulp 105 include disulfide bonds. Disulfide bonds acts like a glue and hold together molecules and proteins. If the disulfide bonds are broken, it may weaken and break down structure of the pulp 105 and facilitate removal of tissues from the pulp 105.

Figure 2:
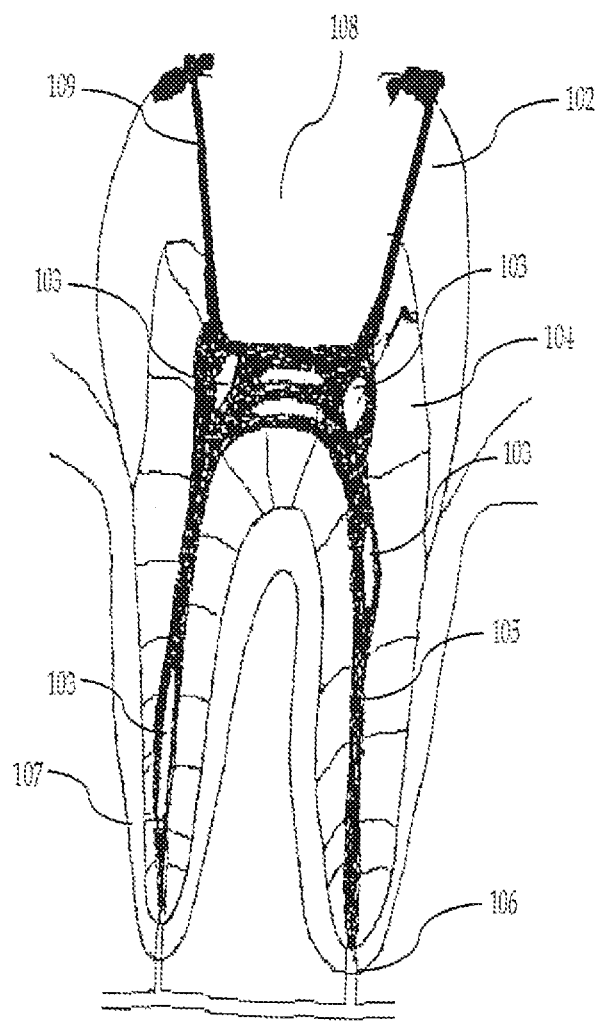
FIG. 2 illustrates the tooth of FIG. 1 at a stage of treatment showing access to the pulpal chamber in accordance with an embodiment of the present invention.

FIG. 2 depicts the tooth 100, during the root canal treatment, according to an embodiment of the present invention. The pulpal chamber is accessed, as shown in the figure. FIG. 2 further depicts access to the cavity 108, and access to cavity walls 109.

Figure 3:
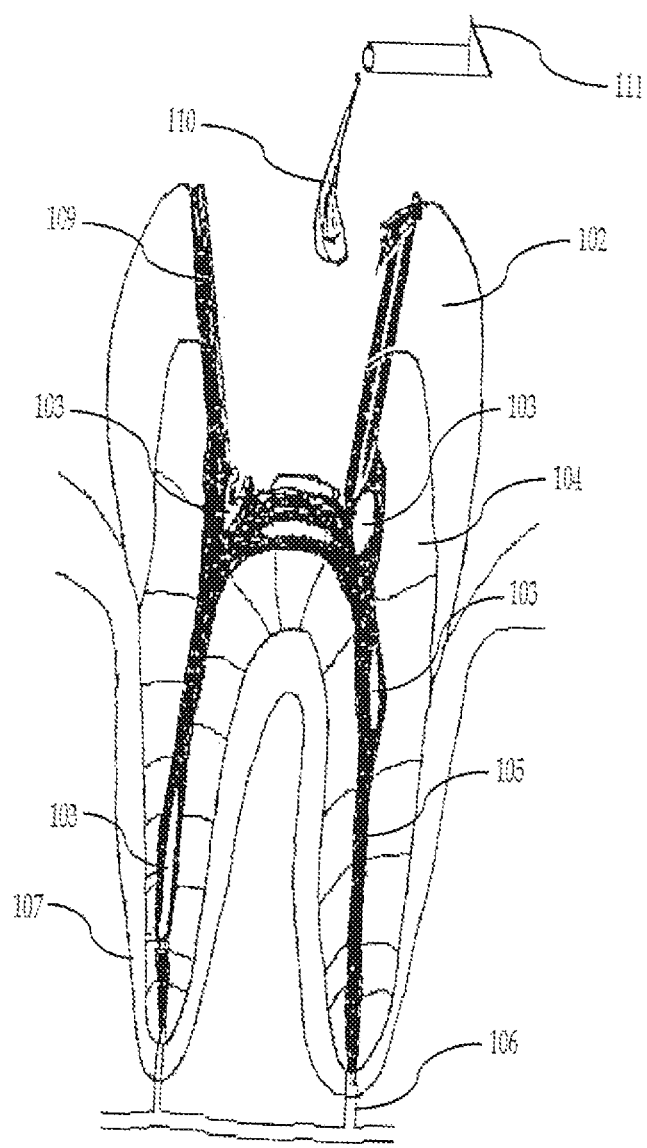
FIG. 3 illustrates the tooth of FIG. 1 at a further stage of treatment showing a composition being applied in accordance with an embodiment of the present invention.

FIG. 3 depicts introduction of a composition 110 into the cavity 108, according to an embodiment of the present invention. The composition is placed into the cavity 108 by using a disposable needle 111.

According to an embodiment of the present invention, the composition 110 is a chemical depilatory. The present invention utilizes the chemical depilatory as an endodontic intracanal medicament for irrigation, disinfection, and lubrication to provide antimicrobial properties and further facilitate removal of the smear layer. In an embodiment of the present invention, the composition 110 breaks the disulfide bonds in the pulpal tissue. The breakage of the disulfide bonds degrades structure of the pulpal tissue in order to remove tissue.

The chemical depilatories have been used for a wide variety of purposes. For example, chemical depilatories have been used for reducing microbial levels on the hide of an animal. Further, the chemical depilatories have been used in removal of hair from skin and outer extremities as from the arms, legs, face, and underarms. Furthermore, the chemical depilatories have been used to remove unwanted hairs from the external skin of both animals and humans. However, chemical depilatories have never been used in endodontics or in dentistry.

Further, tissues of the pulp 105 and hair have a similar characteristic of containing disulfide bonds as both are derived from neural crest stem cells. The hair follicle bulge is derived from cranial neural crest, and similarly the dental pulp and periodontal ligament are derived from the neural crest. Chemical depilatories has been used in hair removal on humans and as an antimicrobial agent on hides of animals for years successfully, the present invention utilizes the chemical depilatories in a novel way for use in endodontic and for removal of tissue from a bony cavity.

According to an embodiment of the present invention, the composition 110 is composed of the following active ingredients: calcium hydroxide, sodium hydroxide, sodium hypochlorite and potassium thioglycolate. In an embodiment of the chemical depilatory composition of the present invention the composition 110 further includes mineral oil, urea, lanolin water, fragrance, cetearyl alcohol and ceteth-20 for contributing to ability of the composition 110 to produce desired results.

According to an embodiment of the present invention, the composition 110 is capable of dislodging calcifications that lie within root canal system by weakening attached connective tissue as well as removal of soft tissue from the cavity of a hard, bony tissue, In an embodiment of the present invention, the composition 110 provides a single endodontic irrigant composition that dissolves tissue, removes the smear layer, and includes antibacterial capability.

Further, in an embodiment of the present invention, the composition 110 (or chemical depilatory) may be used by a dental professional in an unprepared as well as prepared root canal system in order to facilitate the instrumentation of root canal walls and pulpal chamber by dislodging calcificafions, removing pulpal tissue and debris.

The composition 110 may have multiple roles in the root canal treatment. For example, the composition 110 may act as an irrigant, disinfectant, conditioner, antimicrobial agent and lubricant for endodontic chemo-mechanical preparation of the root canal space, according to an embodiment of the present invention.

In various embodiments the composition 110 applied in the, methods according to the present invention includes calcium hydroxide, sodium hydroxide, and potassium thioglycolate, sodium hypochlorite, sodium chloride, oxygen, and sodium chlorate in purified water. Further, in an embodiment of the present invention, the composition 110 may include mineral oil, urea, cetearyl alcohol and ceteth-20 for use for irrigation, disinfection, lubrication, removing the smear layer, dissolving pulpal tissue and as an anti-bacterial agent. In an embodiment of the present invention, the composition 110 may be in the form of, for example, but in not restricted to, a lotion, a cream, a gel, a solution, and a paste. In another embodiment of the present invention, the composition 110 may be an emulsion, such as, microemulsion and macro-emulsion.

Further, in an embodiment of the present invention, lanolin as used as an emollient. Furthermore, in an embodiment of the present invention, water is used for diluting. Further, in an embodiment of the present invention, the composition 110 may also include aloe barbadensis as an emollient.

In an embodiment of the present invention, the composition 110 may be used in endodontic usages during intra-canal instrumentation in order to break disulfide bonds present in pulpal tissue, to remove the smear layer, and to be effective against bacteria present in the root canal system. According to an embodiment, the composition 110 may be used as a single endodontic irrigant on unprepared as well as prepared tooth surfaces in order to dissolve tissue, remove the smear layer, and be effective against bacteria. The composition 110 may further provide for removal of soft tissue inside of a hard, bony cavity. Further, according to an embodiment of the present invention, the composition 110 may provide preparation of regeneration and formation of mineralized and soft tissue in a hard bony cavity (e.g., a human or animal). Furthermore, the composition 110 may be used as intraosseous irrigant, and in medicine, for example, in long bones and in preparing skeletons for museums etc.

Figure 4:
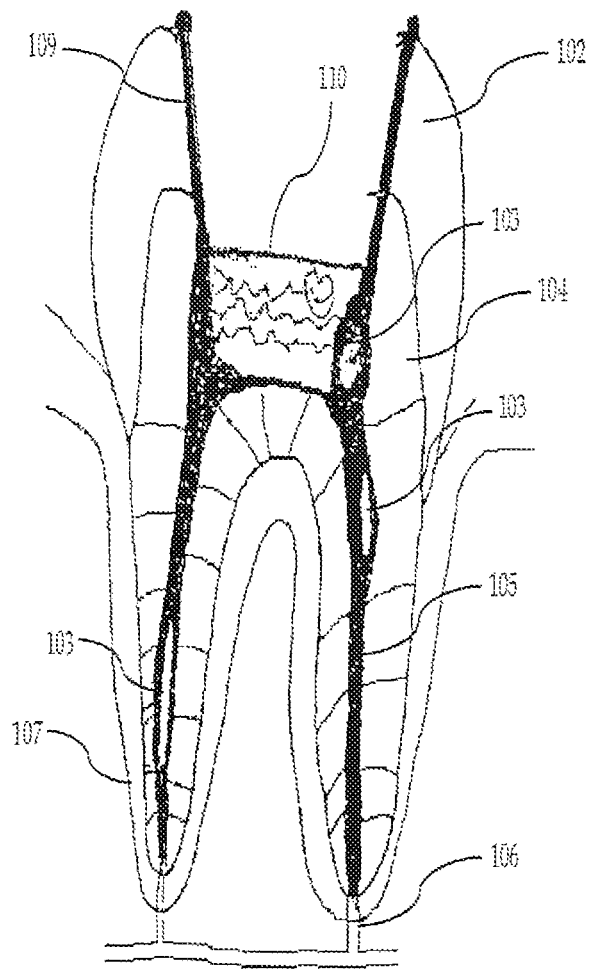
FIG. 4 illustrates the tooth of FIG. 1 at a further stage of treatment showing a composition accessing the cavity's floor in accordance with an embodiment of the present invention.

FIG. 4 depicts the composition 110 accessing the cavity's floor 108 as well as the cavity walls 109. The composition 110 provides removal of soft, connective tissue (i.e., pulp tissues) from within a hard tissue cavity (i.e., enamel and dentin) and hard bony cavities. In an embodiment of the present invention, the composition 110 is a chemical depilatory that removes soft tissue, necrotic tissue, debris, and calcified tissue from within the hard tissue cavity. In an embodiment of the present invention, the composition 110 functions as an intra-canal medicament with properties of an irrigant, disinfectant, lubricant, antimicrobial agent, debriding agent, and cleansing agent (as it is capable of removing the smear layer). The composition 110 is further capable for chemo-mechanical cleansing and enlarging of the root canal system. Furthermore, the composition 110 is also capable of bleaching teeth.

According to an embodiment of the present invention, the composition 110 includes the active ingredients of calcium hydroxide, sodium hydroxide, and potassium thioglycolate, sodium hypochlorite, sodium chloride, oxygen, and sodium chlorate in purified water, as discussed above.

In one, embodiment of the present invention, calcium hydroxide (present in the composition 110) creates an alkaline environment so that endodontic pathogens are not able to survive. Further, in an embodiment of the present invention, sodium hydroxide (which is a strong base) is used in tissue digestion by bleaching. Further, the sodium hydroxide breaks down chemical bonds in tissue as bone remains present. The sodium hypochlorite decomposes to sodium chloride, which interferes with membrane permeability and functioning, and the antiseptic compound sodium chlorate when the depilatory composition is at pH significantly less than 11.

Further, in an embodiment of the present invention, potassium thioglycolate (present in the composition 110) breaks down sulfur bonds present in keratin protein of pulp. Potassium thioglycolate reacts with the cystine present in the protein and can unfold various proteins within 30 seconds. The reaction is following: $2SH-CH_2-COOH$ (thioglycolic acid)$+R-S-S-R$ (cystine=disulfide bridge)$\longrightarrow$ $2R-SH+COOH\ CH_2\ SS\ CH_2\ COOH$ (dithiodiglycolic acid).

Further, in an embodiment of the present invention the composition 110 may include one or more of following constituents including, but not limited to, water, mineral oil, urea, cetearyl alcohol, D&C yellow No. 8, chromium hydroxide, theobroma cocoa seed butter, iron oxides, fragrances, and ceteareth-20. According to an embodiment of the present invention, the mineral oil may fill surface cracks. Those skilled in the art will appreciate that the surface cracks if not filled, may harbor bacteria. Further, the mineral oil may act as a lubricant. Further, according to an embodiment of the present invention, the urea may retain moisture and function as a keratolytic emollient.

Further, according to an, embodiment of the present invention, the cetearyl alcohol may include a coconut oil. The cetearyl alcohol can emulsify with ceterth-20 can to form cetereth-20 and enhances viscosity of the lotion.

Figure 5:
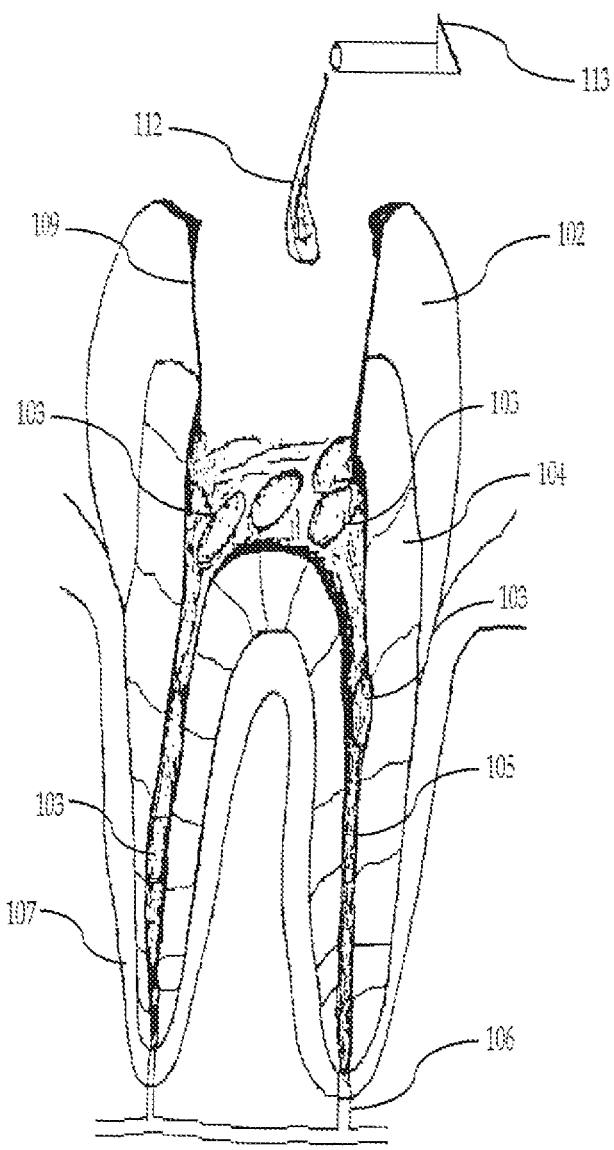
FIG. 5 illustrates the tooth of FIG. 1 at a further stage of treatment showing a rinsing solution in accordance with an embodiment of the present invention.

Once, the pulp has been cleaned out and root canal area disinfected with help of the composition, a rinsing solution may be introduced, as shown in FIG. 5.

Figure 6:
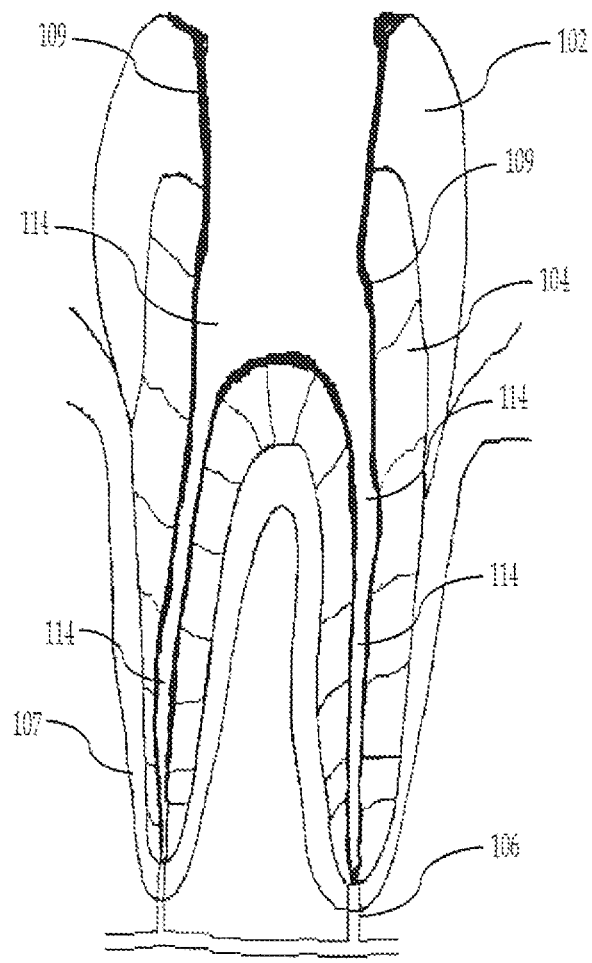
FIG. 6 illustrates the tooth of FIG. 1 at a further stage of treatment, showing the tooth after rinsing and the empty root canal, in accordance with an embodiment of the present invention.

FIG. 5 shows introduction of a rinsing solution 112 using a disposable needle 113 for applying the rinsing solution. FIG. 6 shows the tooth 100 after rinsing with an empty root canal system 114.

According to an embodiment of the present invention, the composition 110 (i.e., the chemical depilatory) breaks the disulfide bonds in the pulpal tissues. Therefore, any pulp stones attached to weakened pulpal tissues can also be removed. The breaking of bonds aids in the removal of unwanted pulpal tissue and debris. The composition 110 further lubricates, irrigates, disinfects, dissolves, cleanses and removes the smear layer. Further, the composition 110 (or the chemical depilatory) provides antimicrobial protection against infections.

The composition 110 includes chemicals (that breaks the disulfide bonds, e.g., calcium hydroxide, sodium hydroxide, and potassium thioglycolate) with other substances (that are needed to lubricate, dissolve, disinfect and, remove pulpal debris, e.g., mineral oil, urea, cetearyl alcohol and ceteth-20). The disulfide bonds are present in myelinated sheath of nerves that enters the tooth via its apical opening. The composition 110 weakens portion of the myelinated sheath of an entering nerve within the root canal system, so that, it can be easily scraped off the inner root canal wall of the tooth. For example, the chemical depilatories removes the hair from the follicle by weakening it at the point that it emerges from the follicle, the present invention utilizes the chemical depilatories in weakening nerve's protection by breaking down the disulfide bond in the myelinated sheath that surrounds and protects the nerve.

Further, the composition 110 provides cleansing and debriding the pulp chamber and root canal space. The composition 110 further removes smear layer by breaking the disulfide bonds present in glycosaminoglycans (GAG), which is the matrix of the inorganic layer Furthermore, the composition 110 provides dislodging pulpal calcifications by breaking bonds within the tissue that surrounds the calcification.

Hence, the composition 110 provides disinfecting, cleansing, irrigating and lubricating both prepared and unprepared tooth surfaces during dental procedures. The composition 110 may be used in endodontic during non-surgical root canal therapy during intra-canal chemo-mechanical preparation. Also, the composition 110 further may be used to remove the debris that is formed during dental procedure and dissolve proteins within the pulpal chamber.

Further, according to embodiment of the present invention, the composition 110 may be used for cleaning, irrigating, disinfecting etc. of inside of any bony cavity (e.g., a hard bony cavity, a bony cavity in canines). For example, the composition may be used for intra-medullary reaming and irrigating (e.g., to be used before a rod n orthopedics), maceration (e.g., cleaning animal skulls & bones used of preserving them), preparing a bony surface for stem cells, for a site for regeneration of new tissue, and for removing tissue from inside a bony cavity to allow for the mineralized tissue.

Further, the composition 110 may be used for preparing a bony surface for cellular differentiation, tissue formation, and tissue regeneration. Those skilled in the art will appreciate that for making regeneration of stem cells successful, the diseased or unwanted cells must be removed as they damage the underlying tissues' ability to generate on its own new cells. In an embodiment of the present invention, the composition 110 removes the diseased or unwanted, infected or inflamed cells, and provides a clean area for regeneration of stem cells.

Further, the composition 110 may assist a dentist to prepare the tooth surface to place stem cells inside the tooth for pulpal and tissue regeneration. The stem cells may be used within the pulpal chamber. For example, an embodiment of the present invention provides a root, canal therapy whereby a root canal procedure will be cleaning the chamber/roots and then placing stein cells to re-grow pulpal and mineralized tissue. Those skilled in the art will appreciate that this can only be performed if the composition 110 as described here in above is first used to clean the inside of the tooth 100, and failure to clean the inside of the tooth 100 sufficiently will not provide a clean enough surface for the placement of stem cells. The composition 110, provided by the present invention, provides cleaning of the inside of the tooth 100 and provides a clean surface for placement of stem cells. Furthermore, according to an embodiment of the present invention, the composition 110 may also provide bleaching of teeth as it removes the dead blood which is dark in color from within the teeth that gives the tooth a dark shade.

Figure 7:
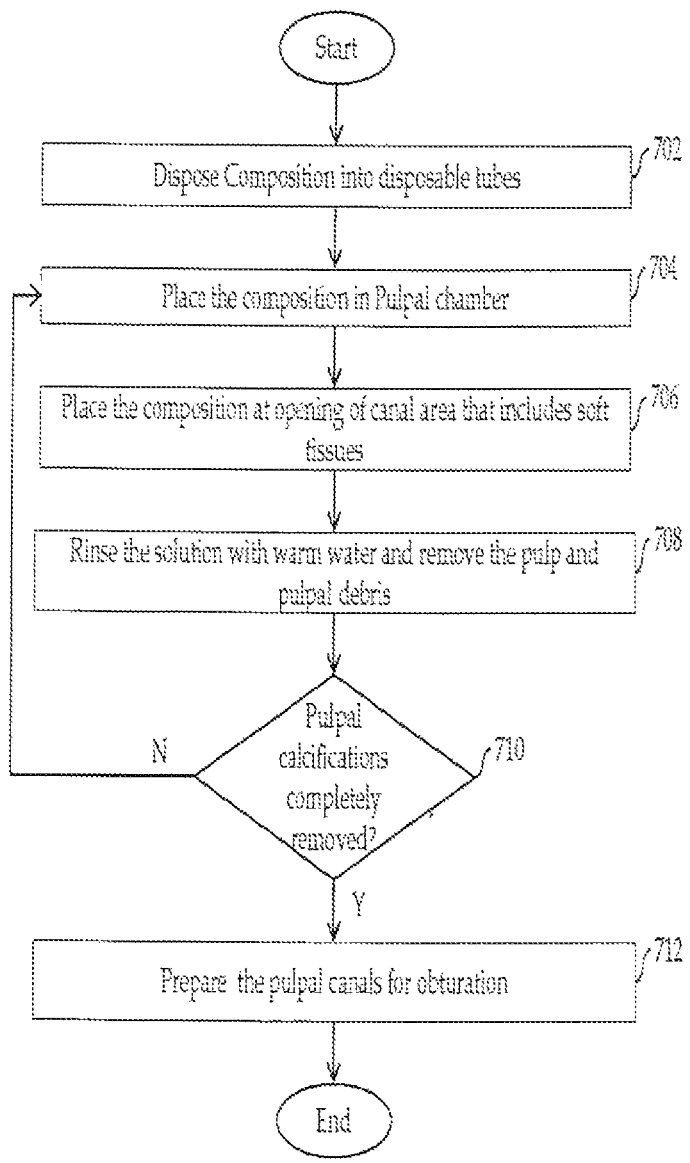
FIG. 7 is a flow chart depicting root canal treatment using a composition, in accordance with an embodiment of the present invention.

FIG. 7 is a flowchart of a method 700 for cleaning out pulp and disinfecting root canal area in a root canal treatment, according to an embodiment of the present invention. According to an embodiment of the present invention, the method 700 provides using a chemical depilatory as a composition in endodontic. The method 700 is effective due to disulfide bonds presence in pulpal tissue.

At step 702, a chemical depilatory composition is dispensed into disposal tubes. Further, disposal needles may be attached to the disposable tubes. According to an embodiment of the present invention, the composition may include sodium chlorate, sodium hydroxide, and potassium thioglycolate. In one embodiment of the present invention, calcium hydroxide (present in the composition) creates an alkaline environment so that endodontic pathogens are not able to survive. Further, in an embodiment of the present invention, sodium hydroxide (which is a strong base) is used in tissue digestion. Further, sodium chlorate is an antiseptic agent. Further, the sodium hydroxide breaks down chemical bonds and further keeps bones intact. Furthermore, in an embodiment of the present invention, potassium thioglycolate (present in the composition) breaks down sulfur bonds present in protein of pulp, tissue. In another embodiment of the present invention, potassium thioglycolate is a thiol-based depilatory.

In another embodiment of the present invention, the composition may further include mineral oil, oxygen, sodium chloride, sodium hypochlorite, urea, cetearyl alcohol, D&C yellow No. 8, chromium hydroxide, theobroma cocoa seed butter, iron oxides, fragrances and ceteareth-20 to enhance its functioning, in addition to calcium hydroxide, sodium hydroxide, sodium hypochlorite and potassium thioglycolate. According to an embodiment of the present invention, the mineral oil may act as a lubricant. Further, according to an embodiment of the present invention, the urea may retain moisture, prevent infections, treat inflammatory conditions, and function as a keratolytic emollient. Further, according to an embodiment of the present invention, the cetearyl alcohol can emulsify with ceterth-20 can to form cetereth-20 and enhances viscosity of the lotion, In an embodiment, the cetearyl alcohol may include a coconut oil. Furthermore, in an embodiment of the present invention, the fragrance acts as deodorizers.

At step 704, a few drops of the composition are placed in a pulpal chamber to wet the floor with the disposable needle. At step 706, the composition or solution is placed it at opening of the canal for going inside the canal with help of an endodontic file/reamer/instrument of choice, coat the 'file' with the solution and. In an embodiment of the present invention, the opening of the canal may include, but is not restricted to, soft tissues. The solution is left there for about 1-3 minutes.

At step 708, the composition or solution is rinsed with warm water. Further, in an embodiment of the present invention, the solution may also be rinsed with warm sodium hypochlorite. In another embodiment of the present invention, the solution may also be rinsed with other commercial, conventional irrigants. Further, the pulp and pulpal debris is removed and irrigated out.

At step 710, it is determined whether the pulpal calcifications or infected/damaged area of tooth has been completely removed and dislodged, and the canal area has been completely disinfected. In case, there are still some tissues of pulp remaining or infection remaining, flow of the method 700 returns to the step 702. Otherwise, the method 700 proceeds towards step 712, wherein the pulpal canal is prepared for obturation. In an embodiment of the present invention, a mechanical instrument procedure may be carried out for obturating the pulpal canal and then the method 700 concludes.

Figure 8:
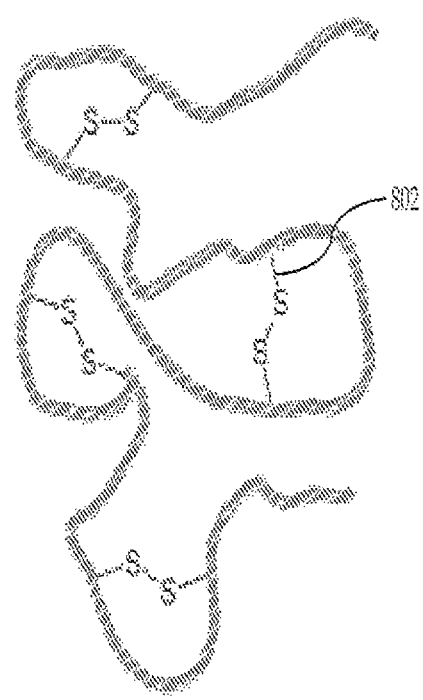
FIG. 8 illustrates structure of disulfide bonds in proteins according to an embodiment of the present invention.

FIG. 8 illustrates disulfide bonds in proteins according to an embodiment of the present invention. Disulfide bonds 802 present in tissue proteins of a human body may be considered as a framework for living cell. In an embodiment of the present invention, in a human body, let say, are infected area having neoplastic cells is present in tissue. By using the present invention the infected area of the human body may be treated by a chemical depilatory that can cause apoptosis in abnormal cells. The present invention applied to the infected area breaks disulfide bonds 802 present. When the disulfide bonds 802 are broken in the infected tissue, a doctor may prevent regeneration of the neoplastic cells in that area. Further, DNA, RNA or proteins are dependent upon the disulfide bonds 802 for their integrity and existence. Therefore, once the disulfide bonds 802 are broken, the cell loses its ability for functioning and regeneration. Cellular breakdown results in the prevention and arrest of abnormally growing cells.

The foregoing disclosure has focused on exemplary depilatory compositions which disrupt disulfide bonds. These exemplary compositions are not intended to be limiting, however, and it should be appreciated that any composition or active pharmaceutical ingredient which effectively reduces such disulfide bonds can fall within the scope of the various systems and methods of the invention. Exemplary active ingredients suitable for use in the various embodiments of the invention include, without limitation, potassium thioglygolate, calcium thioglycolate, 2-mercaptoethanol, dithiotheitol, dithioerythritol, tris(2-carboxyethyl)phosphine, dithiobutylamine, and glutathione, as well as combinations of two or more of these ingredients.

The various methods of the present invention generally involve the application of the compositions described above to contact materials in bony cavities such as the pulpal cavity of a tooth. These compositions are applied, in some cases, by irrigating the bony cavities with flowable compositions that can be delivered through syringes and irrigation needles or flexible tips familiar to those of skill in the art. In other cases, the compositions are pastes that are placed in bony cavities using a spatula and/or by coating an instrument such as an endodontic file with the paste and then using the instrument to mechanically debride the bony cavity. As the examples below demonstrate, the compositions can contact various surfaces within the cavity for intervals normally associated with endodontic irrigation and de-pulping, such as 1, 5, 15 or 30 minutes.

Compositions of the invention are delivered in any suitable format for use in an endodontic or general dental office. In one group of embodiments, a composition is provided in a pre-filled syringe which is optionally packaged with one or more irrigation needles or flexible tips and/or directions for use that set out one of the methods for irrigating a bony cavity discussed above.

Although the foregoing disclosure has focused on examples in the endodontic setting, compositions according to various embodiments of the invention are useful in a variety of other settings. While not wishing to be bound by any theory, in general, compositions of the invention do not degrade "bony" tissues comprising hydroxyapatite (which lacks disulfide bonds), such as tooth or bone. However, non-bony tissues ("soft" tissues) and microbes are generally much more susceptible to disruption. Accordingly, in one group of preferred embodiments, compositions of the invention are disposed within body cavities which are at least partially defined by bony tissues ("bony cavities"). Bony cavities can be naturally occurring, such as the marrow cavity of a bone or the pulpal cavity of a tooth. Alternatively or additionally, bony cavities can be at least partially man made, for instance in the course of operative removal of a carious lesion from a tooth, or due to the resection of tumorous tissue from a bone. With respect to operative treatment for carious lesions in particular, it is believed that methods of the invention advantageously permit the disinfection of bony cavities before they are filled, thus reducing the risk of recurrence of the lesion or of other undesirable sequelae. As the following examples demonstrate, compositions of the invention are, advantageously, effective in, reducing titers of *streptococcus mutans*, which is known to contribute to the formation of carious lesions in teeth.

Compositions of the present invention are also useful for disinfecting bony cavities and surfaces for taxidermy or pathology purposes. In certain embodiments, for instance, a composition of the invention is applied to bony cavities in cadaver skeletons to prepare them for display.

Test Results

Test results will now be provided here to illustrate the above principles. The following example illustrates working of the present invention in accordance with an embodiment of the present invention. A person of ordinary skill in the art will appreciate the present invention may be performed for any medical use and is not limited to any particular medical application.

Testing of the composition according to the present invention's anti-microbial activity was done in an independent laboratory in accordance with the USFDA Regulations 21 CFR Part 58. The testing of the present invention was done under the supervision of a quality assurance supervisor and a study director. The study was done at an off-site laboratory that performed the tests under protocol that includes reproducibility of test results and details to allow for inspection. The laboratory keeps all the documentation and details on file.

Preferred embodiments of the antimicrobial composition for tissue dissolution, disinfection, tissue degradation and tissue removal according to the present invention are composed of the following active ingredients: from, about 0.2% to about 6% sodium hypochlorite (NaOCl), from about 0.5% to 2% of potassium thioglycolate, and about 0.0001 to 8.0% calcium hydroxide in purified water. All the foregoing percentages are by weight.

Test results for the antimicrobial effectiveness of a single exemplary composition according to the invention are reported herein below, although several other exemplary compositions were prepared and tested. The exemplary composition was prepared by mixing about 5.6% sodium hypochlorite, about 1% of potassium thioglycolate, and about 0.01% calcium hydroxide into purified water. The initial pH of this mixture was 7.97, but after three weeks (when the antimicrobial effectiveness was measured) the pH had reached about 6.5. The exemplary composition can be readily used for endodontic applications at these pH values.

However sodium hypochlorite reacts with water at these pHs to form hypochlorous acid, which is unstable and decomposes. Sodium hypochlorite decomposes according to the following two reactions (a) and (b) to form NaCl, $NaClO_3$ and oxygen:

$$3NaOCl \approx 2NaCl + NaClO_3 \tag{a}$$

$$2NaOCl \approx 2NaCl + O_2 \tag{b}$$

As a result of the reactions a and b and approximate known decomposition pathway ratios (a/b is about 9/1), the following chemical species were present in the antimicrobial exemplary composition in the following respective theoretically calculated amounts after three weeks (the time interval between the preparation of the exemplary composition and the tests).

Calculated Amounts of Chemical Species in the Tested Antimicrobial Composition at the Time of the Testing Test Solution 1:

| | |
|---|---|
| Sodium hypochlorite (NaOCl) | 0.3859% |
| Potassium thioglycolate | 1.0120% |
| Calcium hydroxide (Ca(OH)$_2$) | 0.0080% |
| Sodium Chloride (NaCl) | 2.8400% |
| Oxygen | 0.1100% |
| Sodium chlorate (NaClO$_3$) | 2.2200% |
| Purified water | 93.4180% |

*All amounts of chemical species are in weight percent

Test Solution 2:
NaOCl: 5.24%
CaOH: 0.0128%
Potassium thioglycolate: 2.02%
Purified Water: 92.72%

Test Solution 3:
NaOCl: 278%
CaOH: 0.008%
Potassium Thioglycoclate: 1.01%
Purified Water: 96.20%

The testing of the test organisms was performed with respective contact times of 30 seconds, 1 minutes and 2 minutes after introducing the aforesaid exemplary antimicrobial composition. The time intervals were chosen so as to correspond to times that practitioners use in clinical practice. The maximum time was chosen as 2 minutes, since actual treatment time should be below 10 minutes to prevent unwanted dentinal demineralization. Keeping patient's mouth open for 30 minutes maximum for a procedure is reasonable which would allow for amble time for treatment in a tooth with multiple canals. Recovery times were tested for bacteria using 2-5 days times since they are the same for other organisms as *C. albicans* with 2-5 days in. Recovery values are the colonies forming abilities. The testing took place a bout three weeks, after preparation of the exemplary antimicrobial composition.

The plate counts are based on colony formation units (CFU)/plate for *E. facailis* bacteria. For bacteria, the 25-250 CPU/plate are statistically accurate range. Soybean Casein Digest Agar was used as the medium for plates of the test organism of *E. faecalis*. All plates were handled under laboratory conditions with their controls.

The test microorganism was *E. faecalis* because they are the prevalent organisms in Endodontic infections. Endodontic infections are mixed microorganisms or flora. However, *Enterococci faecalis* are the microorganisms that have a major presence in the endodontic lesion, which all need to be eradicated. *E. faecalis* is the organism that has been indicated as the most persistent and prevalent organisms found in endodontic cases that become reinfected. Other microorganisms as *Candida albicans* and *Streptococcus mutan* can be eliminated from the root canal system but *E. faecalis* is the organism that is known to persist. Furthermore, *S. mutans* has a significant presence in root canal infections as, it is known as the organism producing tooth decay, since it has the ability to, survive levels of oxygen tension and absence of essential nutrients. *S. mutans* can maintain microbial growth and continue acid production at low pH values. *S. mutans* and *Candida albicans* can be eliminated in root canal therapy while *E. Faecalis* and is resistant. *Enterococcus faecalis*, bacteria, is found most commonly in persistent radiographic lesions after root canal treatment. Due to the prevalence of *E. faecalis* in persistent endodontic infections, it is essential that the main persistent etiologic agent is eradicated during root canal instrumentation. Therefore, complete removal of irritants from the root anal system is best and most effective way to eradicate root canal infections.

The test procedure for evaluation of products (the anti-microbial composition) for anti-microbial activity against selected organisms at representative contact times is described herein below. Products were evaluated in a liquid matrix. The test organisms and contact times were chosen. This is a quantitative test that allows the determination of the amount of organism reduction at pre-determined intervals. All test method acceptance criteria were met, The acceptance criteria were that negative controls should be negative for growth, positive controls should be positive for growth, and neutralization should be confirmed at about 70%. Specific criteria for pass/fail of the test article were determined.

Inoculum Preparation: Plates of Soybean Casein Digest Agar (SCDA) media were inoculated with stock cultures of the test organisms *E. faecalis* and incubated at 30-35° C. for 18-48 hours. Plates of Sabouraud Dextrose Agar (SDEX) media were inocul ted with stock cultures of the test organism C. Growth was harvested from the surface using a sterile bent glass rod and Physiological Saline Solution 0.9% (DHSS).

Where necessary, culture suspensions were adjusted for the test procedure with PHSS to approximately (about) $10^8$ CFU/ml using visual turbidity.

Test Article Preparation: Test articles were prepared according to the product label or sponsor instructions and were tested without any additional manipulation or dilution.

Neutralization: A 0.1 ml aliquot of the test article was mixed with 9.9 ml Dey-Engley Neutralizer Broth (DEYE). An additional tube of 10 mL of DEYE was prepared as a titer control. The tubes were inoculated with 0.1 ml of a test organism suspension diluted to approximately <10000 then mixed thoroughly. Aliquots from each tube were plated in triplicate onto SCCA and incubated at 30-35 C.° for 2-5 days for *E. faecalis*.

Controls: Positive control tubes containing 10 mL PHSS were prepared. A 0.1 mL aliquot of the test organism was added to each tube. The positive control was assayed at 0 hour and the longest tested time point. The negative control consisted of plating sterile aliquots of applicable liquid media in triplicate and incubating as described in the test procedure.

Test Procedure: Tubes containing 10 mL of each test article were prepared and inoculated with 0.1 mL of the test organism to yield $10^6$ CFU/mL. The test articles were mixed thoroughly.

At 30 seconds, 1 minutes and 2 minutes of exposure, 1.0 mL aliquots of the test suspension were removed and added to 9 mL of neutralizer and serially diluted to produce a 1:100 dilution of test suspension to neutralizer. The tubes were mixed thoroughly. Serial dilutions were made in the appropriate neutralizer and assayed using a standard spread plate method.

All plating was performed in triplicate. Bacterial test articles were plated onto SCDA and incubated at 30-35° C. for 2-5 days.

Quantitative analysis was used to study the anti-microbial activity of the present invention. The following formulas were used by the independent laboratory in preparing their report of the effectiveness of the present invention.

Calculations: The log reduction values were calculated using the following formula: log reduction=$\log_{10} U - \log_{10} C$
wherein, U=Average positive control titer, C=Average recovered counts The percent reduction values were calculated using the following formula: % Reduction=$[1-1/10^{log\ reduction}] \times 100$ The percent neutralization is obtained according to the following equation: % Neutralization=[(Average Sample Count/Plate)/(Average Control Count/Plate)]×100

The Results:

TABLE I

Test Article 1 - *Enterococcus faecalis*

| Identification | Exposure Intervals | Average Control titer (CFU/ml) | Average Test Article Titer (CFU/ml) | Percent Reduction | Log$_{10}$ Reduction |
|---|---|---|---|---|---|
| Control | 2 min | 2.4 × 10(7) | 1.7 × 10$^7$ | ≈28 | ≈0.14 |
| — | 30 sec. | — | <2.0 × 10$^2$ | >99.99916 | >5.08 |

TABLE I-continued

Test Article 1 - *Enterococcus faecalis*

| Identification | Exposure Intervals | Average Control titer (CFU/ml) | Average Test Article Titer (CFU/ml) | Percent Reduction | $Log_{10}$ Reduction |
|---|---|---|---|---|---|
| Sample I | 1 min | $1.1 \times 10^7$ | $<2.0 \times 10^2$ | >99.99916 | >5.08 |
|  | 2 min | — | $<2.0 \times 10^2$ | >99.99916 | >5.08 |

TABLE II

Test Solution 2:

| Identification | Exposure Intervals | Average Control titer (CFU/ml) | Average Test Article Titer (CFU/ml) | Percent Reduction | $Log_{10}$ Reduction |
|---|---|---|---|---|---|
| Control | 2 min | $2.4 \times 10^7$ | $1.7 \times 10$ (7) | 28 | 0.14 |
| — | 30 sec. | — | $<2.0 \times 10^2$ | >99.9916 | >5.08 |
| Sample 2 | 1 min | $2.4 \times 10^7$ | $<2.0 \times 10^2$ | >99.9916 | >5.08 |
|  | 2 min | — | $<2.0 \times 10^2$ | >99.9916 | >5.08 |

TABLE III

TEST SOLUTION 3:
SAMPLE 3:

| | | | |
|---|---|---|---|
| 30 sec & 1 min & 2 min | $<2.0 \times 10$ (2) | >99.9916 | >5.08 |

TABLE IV

Neutralization of Organism *E. facaelis*:

| ORGANISM | Average Control Counts (CFU) | Average Test Article Counts (CFU) | Percent Neutralization |
|---|---|---|---|
| Test Solution 1 | 39 | 35 | 111 |
| Test Sotution 2 | 36 | 35 | 103 |
| Test Solution 3 | 30 | 35 | 86 |

The qualitative analysis, given here, confirms that the present invention is very useful and successful in its ability to disinfect the pulpal chamber from the test microorganism *E. faecalis*. The qualitative analysis for all of the three test solutions at all of the time intervals had a greater than 99.99916% reduction of test microorganism. Neutralization of the microorganisms was successful because all of the percentage for neutralization was over 70% which was needed for confirmation. Furthermore, in the recovery testing, there were colonies forming units in any of the plates with any of the test microorganisms. Therefore, the microorganisms did not regenerate and did not reappear. The lack of the microorganisms present in the recovery results proves that the present invention is able to eradicate all the test materials/microorganisms during the instrumentation.

The above test results demonstrate that the composition, as provided by the present invention, provides anti-microbial activity against above organism *E. faecalis* which is the most resistant organism in recurrent endodontic retreatments. *E. faecalis* is more persistent and difficult to eradicate than *C. albicans*, and *S. mutans*. Further, the tests show that the present invention, composition, or chemical depilatory provides unexpected results proving its useful in endodontic usages for eradicating *E. faecalis* and other microorganisms as *C. albicans* and *S. mutans* in a very short time. Furthermore, the test results prove that the present invention is able to prevent *E. faecalis* from recovering. Therefore, these test results prove that the present invention is novel in its use and have the ability to eradicate microorganisms in endodontic therapies. Further, the test results prove that the present invention is a novel single intra-canal medicament and as an effective bactericidal agent that kills *E. faecalis*.

The present invention may be useful to eradicate the microorganisms from other bony cavities having infections due to one of the microbes or a microorganisms like *E. faecalis*. If a bacteremia resulted after a dental procedure, these microbes y appear in other bony cavities or on orthopedic prosthesis that may benefit from the present invention's bactericidal ability. In canines, their bony cavities in the middle and inner ear can be Infected by bacteria (*Streptococcus*) and/or fungi (*Candida*). Both of these microorganisms can be killed by the present infection.

Further, the test results prove that the present invention was successful in utilizing the chemical depilatory's ability to break disulfide bonds in bacteria and yeast to disrupt the functioning of the infected cells with the microbes. Therefore, disrupting the ability of the bacteria, yeast, and infected cells to function causes the cells to degrade facilitating the removal of tissues. Further, the test results prove that the present invention is able to disrupt the disulfide bonds in living cells and tissues.

Unless explicitly stated otherwise all amounts of chemical compounds and other materials are expressed in % by weight, based on the total amount of material present.

The exemplary systems and methods of this present, invention have been described in relation to a root canal treatment and removal of tissue from within a hard bony structure. However, to avoid unnecessarily obscuring the present invention, the preceding description omits a number of known structures and devices. This omission is not to be construed as a limitation of the scope of the claimed invention. Specific details are set forth to provide an understanding of the present invention. It should however be appreciated that the present invention may be practiced in a variety of ways beyond the specific detail set forth herein.

Also, while the flowcharts have been discussed and illustrated in relation to a particular sequence of events, it should be appreciated that changes, additions, and omissions to this sequence can occur without materially affecting the operation of the present invention.

A number of variations and modifications of the present invention can be used. It would be possible to provide for some features of the present invention without providing others.

While the foregoing is directed to embodiments of the present invention, other and further embodiments of the present invention may be devised without departing from the basic scope thereof. It is understood that various embodiments described herein may be utilized in combination with any other embodiment described, without departing from the scope contained herein. Further, the foregoing description is not intended to be exhaustive or to limit the present invention to the precise form disclosed, Modifications and variations are possible in light of the above teachings or may be acquired from practice of the present invention.

Certain exemplary embodiments may be identified by use of an open-ended list that includes wording to indicate the list items are representative of the embodiments and the list is not intended to represent a closed list exclusive of further embodiments. Such wording may include "e.g.," "etc.," "such as," "for example," "and so forth," "and the like," etc., and other wording as will be apparent from the surrounding context.

No element, act, or instruction used in the description of the present application should be construed as critical or essential to the present invention unless explicitly described as such, Also, as used herein, the article "a" is intended to include one or more items, Where only one item is intended, the term "one" or similar language is used. Further, the terms "any of" followed by a listing of a plurality of items and/or a plurality of categories of items, as used herein, are intended to include "any of," "any combination of," "any multiple of," and/or "any combination of" multiples of the items and/or the categories of items, individually or in conjunction with other items and/or other categories of items.

The present invention, in various embodiments, configurations, and aspects, includes components, methods, processes, systems and/or apparatus substantially as depicted and described herein, including various embodiments, sub-combinations, and subsets thereof. Those of skill in the art will understand how to make and use the present invention after understanding the present disclosure. The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The foregoing discussion of the present invention has been presented for purposes of illustration and description. The foregoing is not intended to limit the present invention to the form or forms disclosed herein. In the foregoing Detailed Description for example, various features of the present invention are grouped together in one or more embodiments, configurations, or aspects for the purpose of streamlining the disclosure. The features of the embodiments, configurations, or aspects of the present invention may be combined in alternate embodiments, configurations, or aspects other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the present invention.

Moreover, though the description of the present invention has included description of one or more embodiments, configurations, or aspects and certain variations and modifications, other variations, combinations and modifications are within the scope of the present invention, e.g., as may be within the skill and knowledge of those in the art, after understanding the present disclosure. It is intended to obtain rights which include alternative embodiments configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of treating a patient, which comprises the steps of:
   (a) irrigating a pulpal cavity of a tooth with a composition, said composition comprising a thioglycolate, sodium hypochlorite, sodium chloride, oxygen, sodium chlorate, calcium hydroxide, and purified water; and
   (b) removing pulpal tissue from the pulpal cavity.

2. The method according to claim 1, wherein the step of irrigating the pulpal cavity includes flowing the composition into the pulpal cavity.

3. The method according, to claim 2, further comprising the step of providing a syringe having a barrel at least partially filled with the composition, wherein flowing the composition into the pulpal cavity includes expelling the composition from the syringe through an endodontic irrigation needle or syringe tip into the pulpal cavity.

4. The method according to claim 1, wherein the step of irrigating the pulpal cavity includes coating a portion of a medical instrument with the composition and inserting the coated portion into the pulpal cavity.

5. The method according to claim 1, wherein the composition is adapted to disrupt a disulfide bond in at least one of the pulpal tissue and a microbe.

6. The method according to claim 1, wherein irrigating the pulpal cavity comprises degrading the pulpal tissue, thereby facilitating the step of removing the pulpal tissue from the pulpal cavity.

7. The method according to claim 1, wherein the composition further comprises at least one additional compound selected from the group consisting of sodium hydroxide, fragrance, lanolin, mineral oil urea, ceteryl alcohol and ceteareth-20.

8. The method according to claim 7, wherein the hydroxide is present in the composition in an amount effective to deprotonate at least one of the thioglycolate and a biomolecule present in a soft tissue.

9. The method according, to claim 1, wherein said composition is made by mixing potassium thioglycolate, sodium hypochlorite and calcium hydroxide with water to form an aqueous mixture and wherein, at least initially on formation, said aqueous mixture contains from about 0.2% to about 6% by weight of sodium hypochlorite, from about 0.05% to about 2% by weight of potassium thioglycolate, and about 0.010 to about 0.005% by weight of calcium hydroxide.

* * * * *